(12) United States Patent
Kim et al.

(10) Patent No.: US 9,428,798 B2
(45) Date of Patent: Aug. 30, 2016

(54) POLYNUCLEOTIDE AND USE THEREOF

(71) Applicant: Samsung Electronics Co., Ltd., Suwon-si, Gyeonggi-do (KR)

(72) Inventors: Sea-hee Kim, Seoul (KR); Joon-ho Kim, Seongnam-si (KR); Joo-won Rhee, Yongin-si (KR); Sun-ok Jung, Seongnam-si (KR); Ko-bong Choi, Osan-si (KR); Kyu-youn Hwang, Seoul (KR)

(73) Assignee: SAMSUNG ELECTRONICS CO., LTD, Suwon-Si (KR)

( * ) Notice: Subject to any disclaimer, the term of this patent is extended or adjusted under 35 U.S.C. 154(b) by 0 days.

(21) Appl. No.: 14/273,790

(22) Filed: May 9, 2014

(65) Prior Publication Data
US 2015/0080241 A1     Mar. 19, 2015

(30) Foreign Application Priority Data
Sep. 16, 2013  (KR) .......................... 10-2013-0111185

(51) Int. Cl.
*C12Q 1/68*   (2006.01)
*C07H 21/02*  (2006.01)

(52) U.S. Cl.
CPC .................................. *C12Q 1/6848* (2013.01)

(58) Field of Classification Search
None
See application file for complete search history.

(56) References Cited

U.S. PATENT DOCUMENTS

| | | | |
|---|---|---|---|
| 6,777,180 B1 | 8/2004 | Fisher et al. | |
| 2007/0026430 A1* | 2/2007 | Andersen | C12Q 1/6813 435/6.18 |
| 2007/0031857 A1* | 2/2007 | Makarov | C12P 19/34 435/6.18 |
| 2007/0128261 A1* | 6/2007 | Woodward | G01N 33/57415 424/448 |
| 2010/0317062 A1 | 12/2010 | Lao et al. | |

FOREIGN PATENT DOCUMENTS

| | | |
|---|---|---|
| KR | 10-2009-0109377 A | 10/2009 |
| KR | 10-2012-0097793 A | 9/2012 |

* cited by examiner

*Primary Examiner* — Nancy T Vogel
(74) *Attorney, Agent, or Firm* — Leydig, Voit & Mayer, Ltd.

(57) ABSTRACT

A polynucleotide comprising a first region the 5' end of which is complementary to a portion of a target nucleic acid, a cleavable second region, a third region having a stem-loop structure, and a fourth region complementary to the 3' end of the first region, and use of the polynucleotide, as well as a composition comprising two such polynucleotides each of which hybridize different strands of a double-stranded target nucleic acid, and methods and kits using the same for amplifying targets.

14 Claims, 5 Drawing Sheets

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic (Forward primer)

<400> SEQUENCE: 1
ccactttgcc tttctctcca                                                    20

<210> SEQ ID NO 2
<211> LENGTH: 36
<212> TYPE: DNA
<213> ORGANISM: Artificial Sequence
<220> FEATURE:
<223> OTHER INFORMATION: Synthetic (Reverse primer)

<400> SEQUENCE: 2
aatatcacac ctgtgaggcc attcatccca tgattc                                  36

<210> SEQ ID NO 3
<211> LENGTH: 36
<212> TYPE: DNA
<213> ORGANISM: Artificial Sequence
<220> FEATURE:
<223> OTHER INFORMATION: Synthetic (Reverse primer)

<400> SEQUENCE: 3
atcacacctg tggagaggcc attcatccca tgattc                                  36

<210> SEQ ID NO 4
<211> LENGTH: 36
<212> TYPE: DNA
<213> ORGANISM: Artificial Sequence
<220> FEATURE:
<223> OTHER INFORMATION: Synthetic (Reverse primer)

<400> SEQUENCE: 4
acacctgtgg agagaaggcc attcatccca tgattc                                  36

<210> SEQ ID NO 5
<211> LENGTH: 36
<212> TYPE: DNA
<213> ORGANISM: Artificial Sequence
<220> FEATURE:
<223> OTHER INFORMATION: Synthetic (Forward primer)

<400> SEQUENCE: 5
tggcctcaca ggtgtgatat tgaagaagat attgcg                                  36

<210> SEQ ID NO 6
<211> LENGTH: 39
<212> TYPE: DNA
<213> ORGANISM: Artificial Sequence
<220> FEATURE:
<223> OTHER INFORMATION: Synthetic (Forward primer)

<400> SEQUENCE: 6
tggcctctcc acaggtgtga tattgaagaa gatattgcg                               39

<210> SEQ ID NO 7
<211> LENGTH: 42
<212> TYPE: DNA
<213> ORGANISM: Artificial Sequence

```
<220> FEATURE:
<223> OTHER INFORMATION: Synthetic (Forward primer)

<400> SEQUENCE: 7
tggccttctc tccacaggtg tgatattgaa gaagatattg cg                    42

<210> SEQ ID NO 8
<211> LENGTH: 21
<212> TYPE: DNA
<213> ORGANISM: Artificial Sequence
<220> FEATURE:
<223> OTHER INFORMATION: Synthetic (Reverse primer)

<400> SEQUENCE: 8
gtccaaactc atcaatgtat c                                          21

<210> SEQ ID NO 9
<211> LENGTH: 27
<212> TYPE: DNA
<213> ORGANISM: Artificial Sequence
<220> FEATURE:
<223> OTHER INFORMATION: Synthetic (Forward primer)

<400> SEQUENCE: 9
ccactttgcc tttctctcca caggtgt                                    27

<210> SEQ ID NO 10
<211> LENGTH: 21
<212> TYPE: DNA
<213> ORGANISM: Artificial Sequence
<220> FEATURE:
<223> OTHER INFORMATION: Synthetic (Reverse primer)

<400> SEQUENCE: 10
ttcttcaata tcacacctgt g                                          21

<210> SEQ ID NO 11
<211> LENGTH: 21
<212> TYPE: DNA
<213> ORGANISM: Artificial Sequence
<220> FEATURE:
<223> OTHER INFORMATION: Synthetic (Reverse primer)

<400> SEQUENCE: 11
ttcaatatca cacctgtgga g                                          21

<210> SEQ ID NO 12
<211> LENGTH: 21
<212> TYPE: DNA
<213> ORGANISM: Artificial Sequence
<220> FEATURE:
<223> OTHER INFORMATION: Synthetic (Reverse primer)

<400> SEQUENCE: 12
aatatcacac ctgtggagag a                                          21

<210> SEQ ID NO 13
<211> LENGTH: 52
<212> TYPE: DNA
<213> ORGANISM: Artificial Sequence
<220> FEATURE:
<223> OTHER INFORMATION: Synthetic (Hot start forward primer)

<400> SEQUENCE: 13
ccactttgcc tttctctcca caggtgtucg gggtatgaat ccccgaacac ct         52
```

```
<210> SEQ ID NO 14
<211> LENGTH: 46
<212> TYPE: DNA
<213> ORGANISM: Artificial Sequence
<220> FEATURE:
<223> OTHER INFORMATION: Synthetic (Hot start reverse primer)

<400> SEQUENCE: 14
ttcttcaata tcacacctgt gucggggtat gaatccccga cacagg            46

<210> SEQ ID NO 15
<211> LENGTH: 46
<212> TYPE: DNA
<213> ORGANISM: Artificial Sequence
<220> FEATURE:
<223> OTHER INFORMATION: Synthetic (Hot start reverse primer)

<400> SEQUENCE: 15
ttcaatatca cacctgtgga gucggggtat gaatccccga ctccac            46

<210> SEQ ID NO 16
<211> LENGTH: 46
<212> TYPE: DNA
<213> ORGANISM: Artificial Sequence
<220> FEATURE:
<223> OTHER INFORMATION: Synthetic (Hot start reverse primer)

<400> SEQUENCE: 16
aatatcacac ctgtggagag aucggggtat gaatccccga tctctc            46
```

POLYNUCLEOTIDE AND USE THEREOF

RELATED APPLICATION

This application claims the benefit of Korean Patent Application No. 10-2013-0111185, filed on Sep. 16, 2013 in the Korean Intellectual Property Office, the disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 3,446 bytes ASCII (Text) file named "715921_ST25.TXT," created May 8, 2014.

BACKGROUND

1. Field

The present disclosure relates to a polynucleotides used for the detection, analysis, and amplification of target nucleic acids.

2. Description of the Related Art

Samples obtained in the medical field are usually small volume samples and present as mixtures containing various kinds of nucleic acids. As a result, it is generally necessary to amplify target nucleic acids present in a sample to obtain a sufficient amount of the target for accurate analysis.

Current methods of target nucleic acid amplification utilizing primers may undesirably produce non-specific reactants through the formation of a primer dimer during the amplification process. Non-specific reactants are problematic in methods for nucleic acid amplification in that the target nucleic acids are not amplified and/or the sensitivity of the target nucleic acids to the amplification is lowered. In polymerase chain reaction (PCR), since the reaction occurs at high temperatures, the specificity of primers used to amplify target nucleic acids is high. However, when a mixture for PCR is manufactured at room temperature, for example, a temperature in a range of about 20° C. to about 25° C., a primer dimer can be easily formed. In order to inhibit such primer dimer formation, a method of 'hot start' nucleic acid amplification has been developed, which impedes the amplification until the temperature goes up. For example, a method of hot start nucleic acid amplification may include an anti-polymerase antibody that non-covalently binds a polymerase to inactivate it at low temperatures. However, since antibodies are used in such a method, the cost is high and there may be problems of mammalian genomic DNA contamination. Additionally, hot start methods present the difficulty of determining whether all the polymerase and anti-polymerase antibody are bound.

Accordingly, there remains a need for the development of a cost effective and improved method of hot start nucleic acid amplification that inhibits the primer dimer formation without an antibody when preparing a PCR mixture at room temperature.

SUMMARY

Provided is a target nucleic acid amplification kit comprising a target nucleic acid sequence and a polynucleotide, wherein the polynucleotide comprising a first region with a 5' terminus complementary to that of a target nucleic acid, a second region positioned 3' of the first region and including a cleavable nucleotide sequence, a third region positioned 3' of the second region and having a stem-loop structure, and a fourth region positioned 3' of the third region comprising a sequence including the 3' terminus of the polynucleotide that is complementary to the sequence of the 3' end of the first region.

Also provided is a method of amplifying a target nucleic acid using the polynucleotide.

Related compositions, kits, and methods are also provided.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, there is a polynucleotide including a first region comprising at least two consecutive nucleotides including the 5'-terminus of the polynucleotide that are complementary to at least two consecutive nucleotides of a first strand of a target nucleic acid; a second region located 3' (downstream) of the first region comprising at least one nucleotide is cleavable; a third region located 3' of the second region that includes a nucleotide sequence with a stem-loop structure; and a fourth region located 3' of the third region comprising at least two consecutive nucleotides that are complementary to at least two consecutive nucleotides of the 3' end of the first region.

At least two consecutive nucleotides from the 5'-terminus of the first region (the 5' terminus of the polynucleotide) may be complementary to at least two consecutive nucleotides (hereinafter referred to as 'nt') of and including the 3'-terminus of the target nucleic acid sequence. The nucleotide sequence of the 5' end of the first region may be, for example, complementary to that of consecutive nucleotides from the 3'-terminus of a target nucleic acid sequence including 3'-terminus nucleotides consisting of 5 nt to 50 nt, 5 nt to 45 nt, 5 nt to 40 nt, 5 nt to 35 nt, 10 nt to 35 nt, 15 nt to 35 nt, or 10 nt to 30 nt. The first region may comprise DNA, RNA, Peptide Nucleic Acid (PNA), Locked Nucleic Acid (LNA), a nucleotide analogue, or any combination thereof.

The first region of the polynucleotide may act as a primer in template-dependent nucleic acid synthesis. The term "primer" used herein refers to a single-stranded oligonucleotide that may serve as an initiation point for template-dependent DNA synthesis under suitable conditions with a suitable temperature and buffer (e.g., four different types of nucleoside triphosphate and a polymerase). The primer may be hybridized or annealed to a region of a template and form a double-stranded structure. The suitable hybridization condition of nucleic acids for forming a double-stranded structure is well known in the art.

The second region may be cleavable by an endonuclease or by heating process. The cleavage may refer to hydrolysis of phosphodiester bonds within nucleotides. The term "endonuclease" used herein refers to an enzyme that cleaves the phosphodiester bond within a polynucleotide chain. The endonuclease may be, for example, an endoribonuclease or a restriction enzyme. The term "ribonuclease (RNase)" used herein refers to a nuclease that catalyzes the degradation of RNA. The term "endoribonuclease" used herein refers to an enzyme that cleaves the phosphodiester bond within a single-stranded or double-stranded RNA chain. The endoribonuclease may comprise RNase A, RNase H, RNase HII, RNase I, RNase III, RNase L, RNase P, RNase PhyM, RNase T1, RNase T2, RNase V1, or RNase V. RNase HII is an endoribonuclease that nicks on a ribonucleotide within DNA double strands. RNase HII may, for example, nick 5' of the ribonucleotide. The endonuclease may be a restriction enzyme. The restriction enzyme is an enzyme that cleaves DNA within or near specific recognition nucleotide sequences known as restriction enzyme recognition sites. The restriction enzyme may be, for example, a nicking enzyme. The nicking enzyme may be an endonuclease that cuts only one strand of a double-stranded polynucleotide. The nicking enzyme may include, for example, Nt.CviPII, Nt.AlwI, Nt.AlwI, Nt.BstNBI, Nb.BsmI, Nb.BsrDI, Nb.BtsI, Nb.BbvCI, Nt.BbvCI, Nt.BspQI, AspCNI, BscGI, BspNCI, BthCI, EcoHI, FinI, FmuI, PspO3I, TsuI, UbaF11I, UnbI, Vpak11AI, BspGI, DrdII, Pfl1108I, UbaPI, PssI, or SdeOSI. The heating process may be performed by incubation at a temperature of 100° C. or above, for example, at a temperature in a range of about 45° C. to about 100° C., about 45° C. to about 90° C., about 45° C. to about 80° C., about 45° C. to about 70° C., about 50° C. to about 70° C., or about 50° C. to about 65° C. For example, the phosphodiester bonds within RNA may be cleaved at a temperature of 100° C. or above, for example, at a temperature in a range of about 45° C. to about 100° C., about 45° C. to about 90° C., about 45° C. to about 80° C., about 45° C. to about 70° C., about 50° C. to about 70° C., or about 50° C. to about 65° C.

The second region of the polynucleotide may be ribonucleic acid (RNA) or deoxyribonucleic acid (DNA). The second region may include a restriction enzyme recognition site. The term "restriction enzyme recognition site" used herein refers to a short sequence in DNA that is recognized by a restriction enzyme and at which site an enzymatic function (e.g., cleaving) may be performed. The second region may have, for example, a length of 1 nt, 2 nt, 3 nt, 4 nt, 5 nt, 6 nt, 7 nt, or 8 nt. The second region may include, for example, DNA, RNA, PNA, LNA, a nucleotide analogue, or any combination thereof. The DNA-including second region may be cleaved by a restriction enzyme. The second region including RNA may be cleaved by an endoribonuclease. When the second region of the polynucleotide is cleaved by an enzyme, the polynucleotide may be nicked thereon.

The third region of the polynucleotide may include a nucleotide sequence having a stem-loop structure in the 3' direction from the 3'-terminus of the second region. The term "stem-loop" as used herein refers to a structure formed by an intramolecular base pairing when a nucleotide sequence is present in a strand, a complementary sequence thereof is present in a reverse direction in the same strand, and a non-complementary sequence is present therebetween in the same strand. The term "stem-loop" may be interchangeable with other terms such as "hairpin" or "hairpin loop".

The length of the nucleotide sequence of the third region may be, for example, in a range of 7 nt to 100 nt, 10 nt to 100 nt, 10 nt to 90 nt, 10 nt to 80 nt, 10 nt to 70 nt, 10 nt to 60 nt, 10 nt to 50 nt, 10 nt to 40 nt, 10 nt to 30 nt, or 10 nt to 20 nt. The third region may include, for example, DNA, RNA, PNA, LNA, a nucleotide analogue, or any combination thereof. The third region may include nucleotides that are complementary to those of the second region, or nucleotides that are not complementary to those of the second region.

At least two consecutive nucleotides of the fourth region in the 3' direction from the 3' end of the third region may be complementary to at least two consecutive nucleotides of the 3' end of the first region. The length of the nucleotide sequence of the fourth region may be, for example, in a range of 2 nt to 50 nt, 3 nt to 45 nt, 4 nt to 40 nt, 5 nt to 35 nt, 5 nt to 30 nt, 5 nt to 25 nt, 5 nt to 20 nt, 5 nt to 15 nt, or 5 nt to 10 nt. The fourth region may include, for example, DNA, RNA, PNA, LNA, a nucleotide analogue, or any combination thereof. The fourth region may be complementary to a fragment or portion of the first region including the 3'-terminus nucleotides of the first region. The nucleotide sequence of the fourth region may be complementary to that of consecutive nucleotides including the 3'-end nucleotides of the first region, consisting of 2 nt to 50 nt, 3 nt to 45 nt, 4 nt to 40 nt, 5 nt to 35 nt, 5 nt to 30 nt, 5 nt to 25 nt, 5 nt to 20 nt, 5 nt to 15 nt, or 5 nt to 10 nt. The fourth region may be hybridized to the first region. For example, the fourth region may be hybridized to the first region at a temperature in a range of about 0° C. to about 50° C., about 4° C. to about 50° C., about 10° C. to about 50° C., about 15° C. to about 50° C., about 20° C. to about 50° C., about 20° C. to about 45° C., or about 20° C. to about 40° C. The hybridized first region and the fourth region may be denatured at a temperature in a range of about 50° C. to about 100° C., about 50° C. to about 90° C., about 50° C. to about 80° C., about 50° C. to about 70° C., or about 50° C. to about 60° C. As used herein, "denaturation" may refer to the separation of double strands into two single strands.

The 3'-terminus of the fourth region, which is the 3' terminus of the polynucleotide, may be chemically modified. For example, the 3'-terminus nucleotides of the fourth region may include a nucleic acid from which a hydroxyl group is removed, an inverted nucleotide, a dideoxynucleotide, a C6 amine, a C3 spacer, a C6 spacer, a C12 spacer, or any combination thereof. The fourth region may act as a blocking sequence that inhibits extension of nucleic acids by a polymerase.

The first region of the polynucleotide may be connected to the second region of the polynucleotide via a phosphodiester bond. The second region of the polynucleotide may be connected to the third region of the polynucleotide via a phosphodiester bond. The third region of the polynucleotide may be connected to the fourth region of the polynucleotide via a phosphodiester bond. The terms "target DNA", "target RNA", "target nucleic acid", "target nucleic acid sequence", "template" or "target nucleic acid sequence" used herein refer to a nucleic acid that is subject to DNA amplification. The target nucleic acid sequence may be provided as a template for the amplification in a PCR reaction or reverse-PCR reaction. The target nucleic acid sequence may include natural molecules and synthetic molecules. The target nucleic acid sequence may include, for example, genomic DNA or genomic RNA. The target nucleic acid sequence may include DNA, RNA, or a chimera of DNA and RNA. The target nucleic acid may be single-stranded or double-stranded. The length of the nucleotide sequence of the target nucleic acid may have any suitable length, e.g., about 15 nt to 200 nt, 15 nt to 180 nt, 15 nt to 150 nt, 15 nt to 130 nt, 15 nt to 100 nt, 15 nt to 80 nt, 15 nt to 50 nt, 15 nt to 40 nt, or 15 nt to 30 nt.

According to another aspect of the present invention, there is provided a composition useful for amplifying a target nucleic acid, the composition including a first polynucleotide and a second polynucleotide. The first polynucleotide includes a first region comprising at least two consecutive nucleotides including the 5'-terminus of the polynucleotide that are complementary to at least two consecutive nucleotides of a first strand of the target nucleic acid, a second region located 3' of the first region and comprising at least one cleavable nucleotide sequence, a third region 3' of the second region that includes a nucleotide sequence with a stem-loop structure, and a fourth region 3' of the third region and comprising at least two consecutive nucleotides complementary to at least two consecutive nucleotides of the 3'-end of the first region. The second polynucleotide of the composition includes a first region comprising at least two consecutive nucleotides including the 5'-terminus that are complementary to at least two consecutive nucleotides of a second strand of the target nucleic acid, a second region 3' of the first region and comprising at least one cleavable nucleotide sequence, a third region 3' of the second region that includes a nucleotide sequence with a stem-loop structure, and a fourth region 3' of the third region that includes at least two consecutive nucleotides that are complementary to at least two consecutive nucleotides of the 3'-end of the first region.

In one embodiment, the first and second regions of the target nucleic acid are not separated.

Other aspects of the kit, the first region, the second region, the third region, the fourth region, the polynucleotide including these regions, and the target nucleic acid are the same as described, above.

When combined with a target, the first region of the first polynucleotide may be hybridized to the first strand of the target nucleic acid. The first region of the second polynucleotide may be hybridized to the second strand of the target nucleic acid. The first region of the first polynucleotide and the first region of the second polynucleotide may act as a primer set. The primer is the same as described above. The primer set may include a forward primer and a reverse primer.

The amplification process may be any suitable method known for the amplification of nucleic acid. The amplification of the nucleic acid may be, for example, DNA amplification or RNA amplification. The amplification process may be performed under thermal cycling or isothermal conditions. The amplification method may include a polymerase chain reaction (PCR). The amplification may refer to a method of creating multiple copies of target nucleic acid sequences or complementary sequences thereof. For example, the amplification of the target nucleic acid may repeat denaturation, annealing, and extension (or elongation) processes. The term "annealing" used herein may be interchangeable with the term "hybridization". The term "PCR" used herein refers to a method of amplifying a target nucleic acid from primer pairs specifically binding to the target acid by using a polymerase. The PCR may be a hot start PCR.

The composition may further include other well-known materials required for the amplification of the target nucleic acid. For example, the composition may further include a target nucleic acid, a nucleic acid polymerase, a buffer necessary for activity of the nucleic acid polymerase, a cofactor, and/or a substrate. The nucleic acid polymerase may be DNA polymerase, RNA polymerase, reverse transcriptase, or any combination thereof.

According to another aspect of the present invention, provided is a kit for amplifying a target nucleic acid, the kit including a first polynucleotide and a second polynucleotide, as described above with respect to the composition of the invention, and a target nucleic acid sequence or a nucleic acid polymerase. The kit may further include other materials known to be necessary for the amplification of a target nucleic acid. For example, the kit may further include a buffer necessary for activity of the nucleic acid polymerase, a cofactor, and/or a substrate. The nucleic acid polymerase may be DNA polymerase, RNA polymerase, reverse transcriptase, or any combination thereof. In addition, the kit may further include an instruction to be used for the amplification of the target nucleic acid. The nucleic acid polymerase and all other aspects of the kit are as previously described with respect to the other embodiments of the invention According to another aspect of the present invention, provided is a method of amplifying a target nucleic acid, the method comprising first incubating or heating a first polynucleotide and a second polynucleotide, as described herein, in the presence of an endonuclease. The method further comprises incubating or heating the first incubated or heated first and second polynucleotides (first incubated or heated reactants) to cleave the second regions of the polynucleotides to form a single-stranded first region of the first polynucleotide and a single-stranded first region of the second polynucleotide, and incubating the single-stranded first region of the first polynucleotide, the single-stranded first region of the second polynucleotide, and the target nucleic acid to prepare a hybridized product. Thereafter, the method comprises incubating the hybridized product in the presence of nucleic acid polymerase to amplify the target nucleic acid. All other aspects of the method, including the first polynucleotide, the second polynucleotide, the endonuclease, and the target nucleic acid, are as described above with respect to other embodiments of the invention.

The incubating process may be performed under conditions appropriate for maintaining the activity of the endonuclease. The incubation temperature and time may be appropriately selected according to the endonuclease. For example, the incubation process may be performed at a temperature in a range of about 10° C. to about 50° C., about 15° C. to about 45° C., about 20° C. to about 40° C., or about 25° C. to about 40° C. In the case of using RNase HII, the incubation may be performed, for example, at a temperature of 37° C. The incubation may be performed, for example, for about 10 minutes to about 12 hours (overnight).

The heating process may be performed at a temperature of 100° C. or greater, for example, at a temperature in a range of about 45° C. to about 100° C., about 45° C. to about 90° C., about 45° C. to about 80° C., about 45° C. to about 70° C., about 50° C. to about 70° C., or about 50° C. to about 65° C.

The incubation of a first polynucleotide and a second polynucleotide in the presence of an endonuclease, or the heating of a first polynucleotide and a second polynucleotide may nick on second regions of the first polynucleotide and the second polynucleotide. As used herein "nicking" may refer to cleaving of the phosphodiester bond of a polynucleotide.

The method includes heating of the incubated or heated reactant to form a single-stranded first region of the first polynucleotide and a single-stranded first region of the second polynucleotide. The incubated or heated reactant may include the first polynucleotide and the second polynucleotide which have the nicked second regions thereof.

The heating process may be performed, for example, at a temperature of 100° C. or above, for example, at a temperature in a range of about 50° C. to about 100° C., about 50° C. to about 90° C., about 50° C. to about 80° C., about 50° C. to about 70° C., or about 50° C. to about 60° C. Via the heating process, the first region and the fourth region of the first polynucleotide may be denatured, and accordingly the first region may be separated therefrom. Via the heating process, the first region and the fourth region of the second polynucleotide may be denatured, and accordingly the first region may be separated therefrom. The first region separated from the first polynucleotide and the first region separated from the second polynucleotide may act as a primer set.

The method includes incubating the single-stranded first region of the first polynucleotide, the single-stranded first region of the second polynucleotide, and the target nucleic acid to prepare a hybridized product. The hybridization process may be performed using any suitable method. For example, the hybridization process may be performed by incubating the polynucleotide and the target nucleic acid in a known buffer appropriate for the hybridization of nucleic acids. The hybridization process may be performed at an appropriate temperature, for example, a temperature in a range of about 0° C. to about 25° C., or at a temperature of about 4° C. The hybridization temperature may be appropriately adjusted according to the sequences and lengths of a selected polynucleotide and a target nucleic acid. The hybridization process may be performed for an appropriate time period, for example, about 1 to about 12 hours (overnight).

The method includes incubating of the hybridized product in the presence of the nucleic acid polymerase to amplify the target nucleic acid. The amplification process may refer to synthesis of a nucleotide sequence complementary to the target nucleic acid. The amplification process may be any method known for the amplification of nucleic acid. The amplification of the nucleic acid may be, for example, DNA amplification or RNA amplification. The amplification process may be performed under thermal cycling or isothermal conditions. The amplification method may include a polymerase chain reaction (PCR). The amplification may refer to a method for creating multiple copies of target nucleic acid sequences or complementary sequences of the target nucleic acid sequences. For example, the amplification of the target nucleic acid may repeat processes of denaturation, annealing, and extension (or elongation). The term "annealing" may be used interchangeably with the term "hybridization". The term "PCR" used herein may refer to a method of amplifying a target nucleic acid from primer pairs specifically binding to the target acid by using a polymerase. The PCR may be a hot start PCR. The hot start PCR is one form of PCR which inhibits a non-specific amplification product. The PCR may be a multiplex PCR. Multiplex PCR refers to a PCR performing multiple primer sets within a single, identical chamber simultaneously.

Hereinafter, one or more embodiments of the present invention concept will now be described in detail with reference to the following examples. However, these examples are not intended to limit the scope of the one or more embodiments of the present invention.

Example 1

Figure 1:
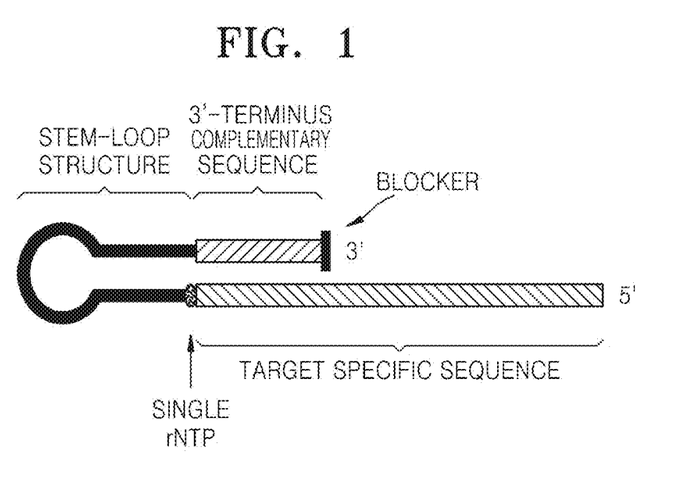
FIG. 1 is a schematic diagram illustrating a hot start primer for amplifying a nucleic acid.
Figure 2:
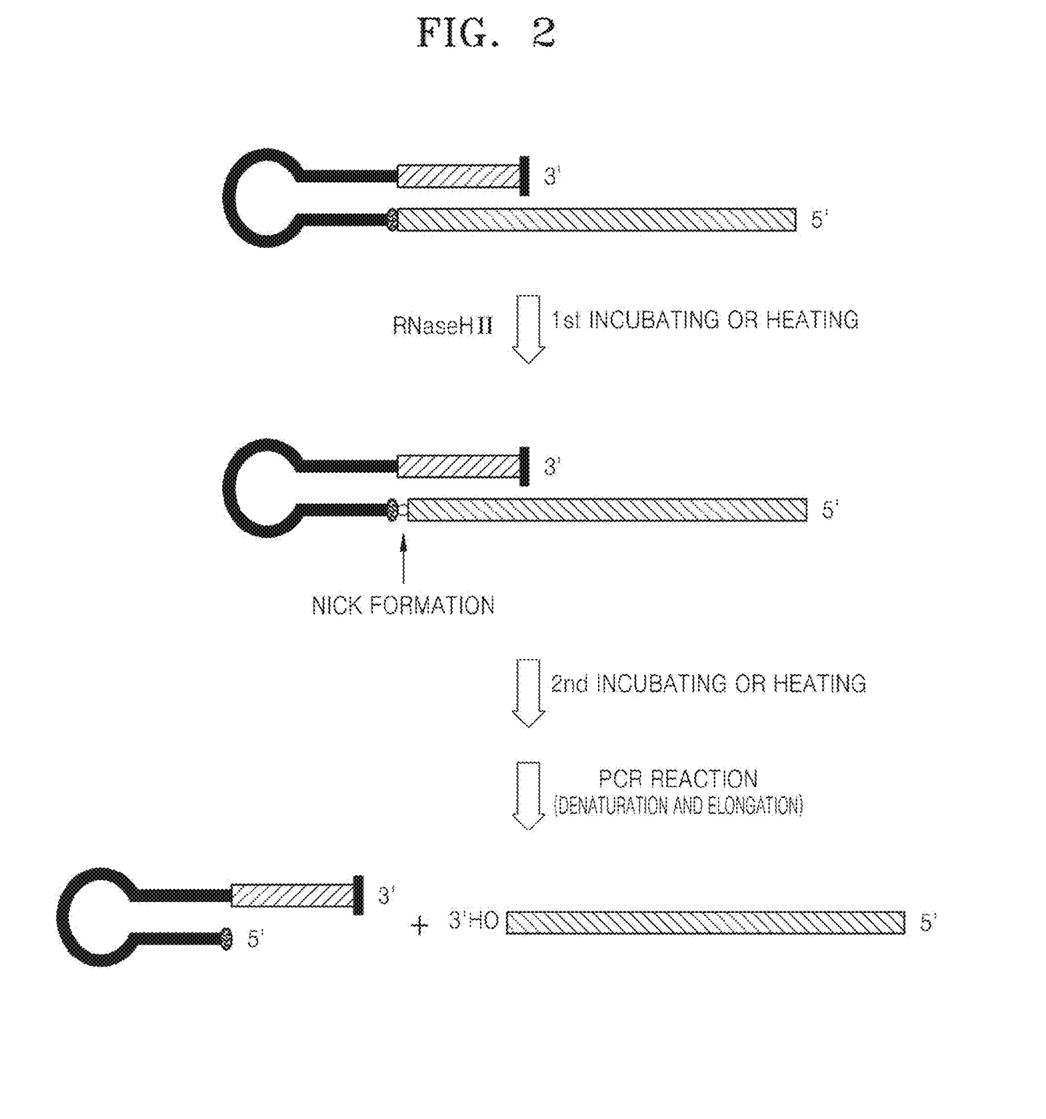
FIG. 2 is a schematic diagram illustrating the mechanism of action of a hot-start primer.
Figure 3:
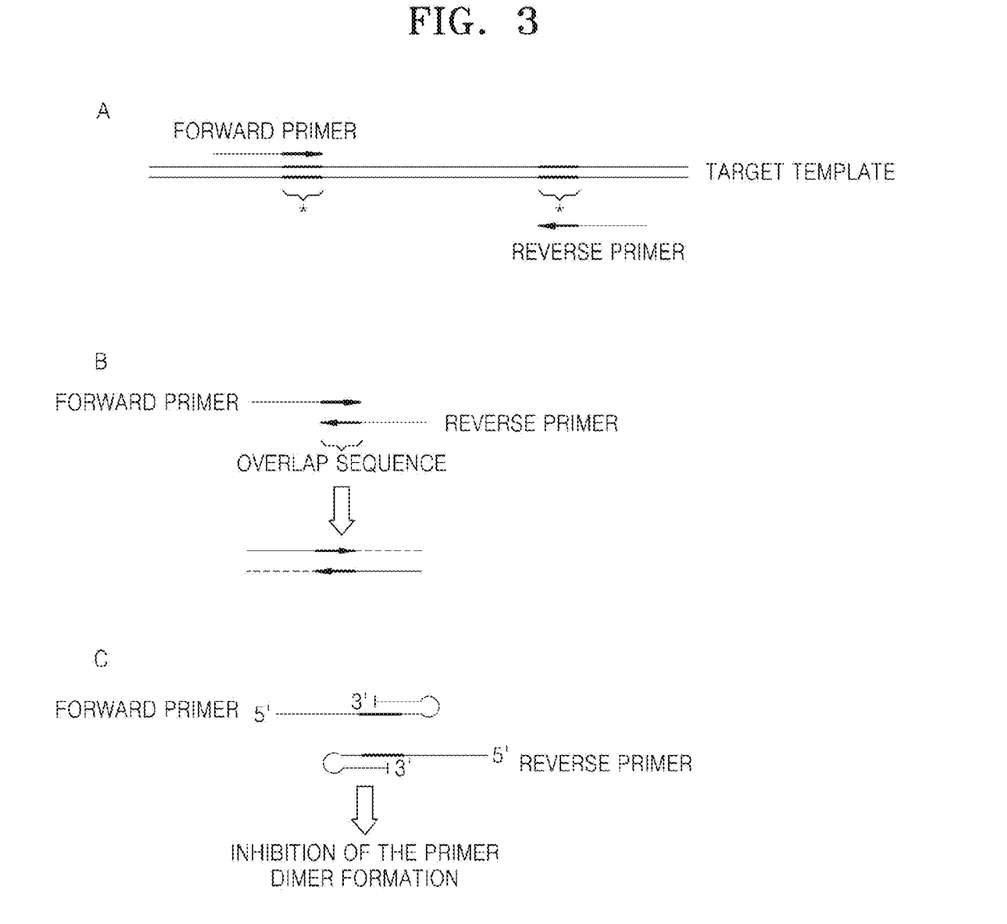
FIG. 3 is a schematic diagram illustrating (A) a target template including an identical nucleotide sequence repeated within the target template; (B) the generation of a non-specific amplification product by forming a primer dimer, wherein each 3'-terminus region of the primer are complementary to each other; and (C) the formation of double strands to inhibit the primer dimer formation.

Preparation of a Target DNA Containing Overlapping Sequences of 9 Base Pairs, 12 Base Pairs, or 15 Base Pairs In order to create suitable conditions for the formation of non-specific amplification products by a primer dimer, a target nucleic acid containing overlapping sequences of 9 base pairs, 12 base pairs, or 15 base pairs was prepared as shown in FIG. 3A.

A PCR mixture in a total amount of 100 μl was prepared according to Tables 1 and 2 below. Here, a pRL-CMV vector (Promega) was used as a template DNA.

TABLE 1

| | Composition | Amount |
|---|---|---|
| Template DNA | pRL-CMV vector (20 ng/μl) | 1 μl |
| Forward primer | pRL-CMV-973-up (100 pmol/μl) | 1 μl |
| Reverse primer | pRL-CMV-9 overlap-R, pRL-CMV-12 overlap-R, or pRL-CMV-15 overlap-R (100 pmol/μl) | 1 μl |
| | 2X HS primer taq mix(Genet Bio) | 50 μl |
| | Distilled water | 47 μl |

TABLE 2

| | Composition | Amount |
|---|---|---|
| Template DNA | pRL-CMV vector (20 ng/μl) | 1 μl |
| Forward primer | pRL-CMV-9bp overlap-F, pRL-CMV-12bp overlap-F, or pRL-CMV-15bp overlap-R (100 pmol/μl) | 1 μl |
| Reverse primer | pRL-CMV-2057-down (100 pmol/μl) | 1 μl |
| | 2X HS primer taq mix(Genet Bio) | 50 μl |
| | Distilled water | 47 μl |

The primer sequences used herein are as follows, and sequences indicated in bold letters represent overlapping sequences.

pRL-CMV-973-up:

(SEQ ID NO: 1)
5'-CCACTTTGCCTTTCTCTCCA-3' pRL-CMV-9bp overlap-R:

(SEQ ID NO: 2)
5'-ATATCACACCTGTGAGGCCATTCATCCCATGATTC-3' pRL-CMV-12bp overlap-R:

(SEQ ID NO: 3)
5'-ATCACACCTGTGGAGAGGCCATTCATCCCATGATTC-3' pRL-CMV-15bp overlap-R:

(SEQ ID NO: 4)
5'-ACACCTGTGGAGAGAAGGCCATTCATCCCATGATTC-3' pRL-CMV-9bp overlap-F:

(SEQ ID NO: 5)
5'-TGGCCTCACAGGTGTGATATTGAAGAAGATATTGCG-3' pRL-CMV-12bp overlap-F:

(SEQ ID NO: 6)
5'-TGGCCTCTCCACAGGTGTGATATTGAAGAAGATATTGCG-3' pRL-CMV-15bp overlap-F:

(SEQ ID NO: 7)
5'-TGGCCTTCTCTCCACAGGTGTGATATTGAAGAAGATATTGCG-3' pRL-CMV-2057-down:

(SEQ ID NO: 8)
5'-GTCCAAACTCATCAATGTATC-3'

The PCR mixture of Tables 1 or 2 was incubated for 10 minutes at 94° C., incubated according to a thermal cycling 30 times consisting of 30 seconds at 94° C., 30 seconds at 55° C., and 30 seconds at 72° C., and incubated again for 5 minutes at 72° C. As a result, a template DNA was amplified. The amplified nucleic acids were purified from the amplified reactant by using a QIAquick PCR purification kit (Qiagen).

A PCR mixture in a total amount of 100 µg was prepared according to Table 3 below by using Template A obtained from the PCR mixture of Table 1 and Template B obtained from the PCR mixture of Table 2.

TABLE 3

| | Composition | Amount |
|---|---|---|
| Template DNA | Template A (50 ng/µl) | 0.5 µl |
| | Template B (50 ng/µl) | 0.5 µl |
| Forward primer | pRL-CMV-973-up (100 pmol/µl): | 1 µl |
| Reverse primer | pRL-CMV-2057-down (100 pmol/µl) | 1 µl |
| | 2X HS primer taq mix(Genet Bio) | 50 µl |
| | Distilled water | 47 µl |

Figure 4:
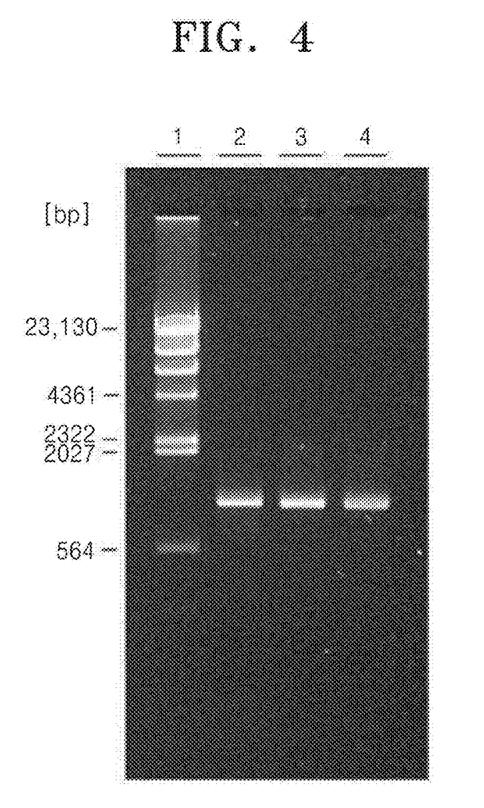
FIG. 4 is a gel electrophoresis separation showing the results of preparation of target DNA including overlap sequences having lengths of 9 nt, 12 nt, or 15 nt wherein lane 1: a size marker, lane 2: a 9 bp overlap template, lane 3: a 12 bp overlap template, and lane 4: a 15 bp overlap template.

The PCR mixture of Table 3 above was incubated for 10 minutes at 94° C., incubated according to a thermal cycling 30 times consisting of 30 seconds at 94° C., 30 seconds at 55° C., and 1 minute at 72° C., and incubated again for 5 minutes at 72° C. As a result, a template DNA was amplified. The amplified reactant was then subjected to electrophoresis for 25 minutes at 100 V in a 1% agarose gel. The electrophoresed gel was dyed with Nucleic Acid Gel Stain (Invitrogen) for 10 minutes, and the results thereof are shown in FIG. 4.

Bands were cut out in a desired size from the gel, and the amplified DNA was purified from the bands by using a QIAquick Gel Extraction Kit (Qiagen). Here, a 9-bp overlapping template (see lane 2 of FIG. 4) having a total length of 1094 bp, a 12-bp overlapping template (see lane 3 of FIG. 4) in a total length 1097 bp, and a 15-bp overlapping template (see lane 4 of FIG. 4) in a total length of 1100 bp were prepared.

Example 2

Amplification of a Target DNA Using a Hot Start Primer 2-1. Preparation of Primers
Primers having sequences below were prepared.

TABLE 4

| Primer | | | Sequence |
|---|---|---|---|
| Normal primer | Forward primer | pRL-CMV-973-F | 5'-CCACTTTGCCTTTCT CTCCACAGGTGT-3' (SEQ ID NO: 9) |
| | Reverse primer | pRL-CMV_1550-90L-R | 5'-TTCTTCAATATCACA CCTGTG-3' (SEQ ID NO: 10) |
| | | pRL-CMV_1550-120L-R | 5'-TTCAATATCACACCT GTGGAG-3' SEQ ID NO: 11) |
| | | pRL-CMV_1550-150L-R | 5'-AATATCACACCTGTG GAGAGA-3' (SEQ ID NO: 12) |
| Hot start primer | Forward primer | pRL-CMV_973-HS_F | 5'-CCACTTTGCCTTTCT CTCCACAGGTGTUCGGGG TATGAATCCCCGAACACC T-3' (SEQ ID NO: 13) |
| | Reverse primer | pRL-CMV_1550-90L-HS(S)_R | 5'-TTCTTCAATATCACA CCTGTGUCGGGGTATGAA TCCCCGAACAGG-3' (SEQ ID NO: 14) |
| | | pRL-CMV_1550-120L-HS(S)_R | 5'-TTCAATATCACACCT GTGGAGUCGGGGTATGAA TCCCCGACTCCAC-3' (SEQ ID NO: 15) |
| | | pRL-CMV_1550-150L-HS(S)_R | 5'-AATATCACACCTGTG GAGAGAUCGGGGTATGAA TCCCCGATCTCTC-3' (SEQ ID NO: 16) |

Sequences indicated in normal letters represent target-specific sequences, sequences indicated in bold letters represent sequences having a stem-loop structure, sequences which are underlined represent RNA, and sequences indicated in italics represent complementary sequence to the target-specific sequences.

2-2. Formation of Nick on Hot Start Primer

In order to nick on a hot start primer, a mixture in a total amount of 10 µl was prepared according to Table 5 below. The prepared mixture was incubated for 30 minutes at 37° C. Here, hot start primers having SEQ ID NO: 13 to SEQ ID NO: 16 were used.

TABLE 5

| Composition | Amount |
|---|---|
| Hot start primer (100 pmol/µl) | 1.0 µl |
| 10x ThermoPol buffer (New England Biolabs) | 1.0 µl |
| RNase HII (New England Biolabs) | 0.5 µl |
| Distilled water | 7.5 µl |

2-3. Amplification of PCR

In order to confirm whether the hot start primer had formed a primer dimer and a non-specific reaction had occurred, PCR was performed using a Taq polymerase.

In order to differentiate the non-specific amplification product by the primer dimer from the target-specific amplification product, the target-specific amplification products were designed such that a target-specific amplification product from the 9-bp overlapping template had a length of 637 bp, a target-specific amplification product from the 12-bp overlapping template had a length of 640 bp, and a target-specific amplification product from the 15-bp overlapping template had a length of 643 bp. Here, a normal primer having SEQ ID NOs: 9-12 was used as a control group.

In the amplification reaction using the normal primer, a primer set consisting of the forward primer and the reverse primer that was used in the 9-bp overlapping template had a primer having SEQ ID NO: 9 and a primer having SEQ ID NO: 10 a primer set consisting of the forward primer and the reverse primer that was used in the 12-bp overlapping template had a primer having SEQ ID NO: 9 and a primer having SEQ ID NO: 11, and a primer set consisting of the forward primer and the reverse primer that was used in the 15-bp overlapping template had a primer having SEQ ID NO: 9 and a primer having SEQ ID NO: 12.

In the amplification reaction using the hot start primer, a primer set consisting of the forward primer and the reverse primer that was used in the 9-bp overlapping template had a primer having SEQ ID NO: 13 and a primer having SEQ ID NO: 14, a primer set consisting of the forward primer and the reverse primer that was used in the 12-bp overlapping template had a primer having SEQ ID NO: 13 and a primer having SEQ ID NO: 15, and a primer set consisting of the forward primer and the reverse primer that was used in the 15-bp overlapping template had a primer having SEQ ID NO: 13 and a primer having SEQ ID NO: 16.

A PCR mixture in a total amount of 20 µl was prepared according to Table 6 below.

TABLE 6

| Composition | Amount |
| --- | --- |
| Taq DNA polymerase (5 unit/µl) (Bioneer Corp.) | 0.5 µl |
| Overlapping template (10 ng/µl) | 1.0 µl |
| Forward primer (10 pmol/µl) | 1.0 µl |
| Reverse primer (10 pmol/µl) | 1.0 µl |
| 10 mM dNTP mixture | 2.0 µl |
| 20 mM MgCl$_2$ | 2.0 µl |
| 10x PCR buffer (Bioneer Corp.) | 2.0 µl |
| Distilled water | 10.5 µl |

The PCR mixture of Table 6 above was incubated for 10 minutes at 94° C., incubated according to a thermal cycling 30 times consisting of 30 seconds at 94° C., 30 seconds at 55° C., and 1 minute at 72° C., and incubated again for 5 minutes at 72° C. As a result, a template DNA was amplified.

Figure 5:
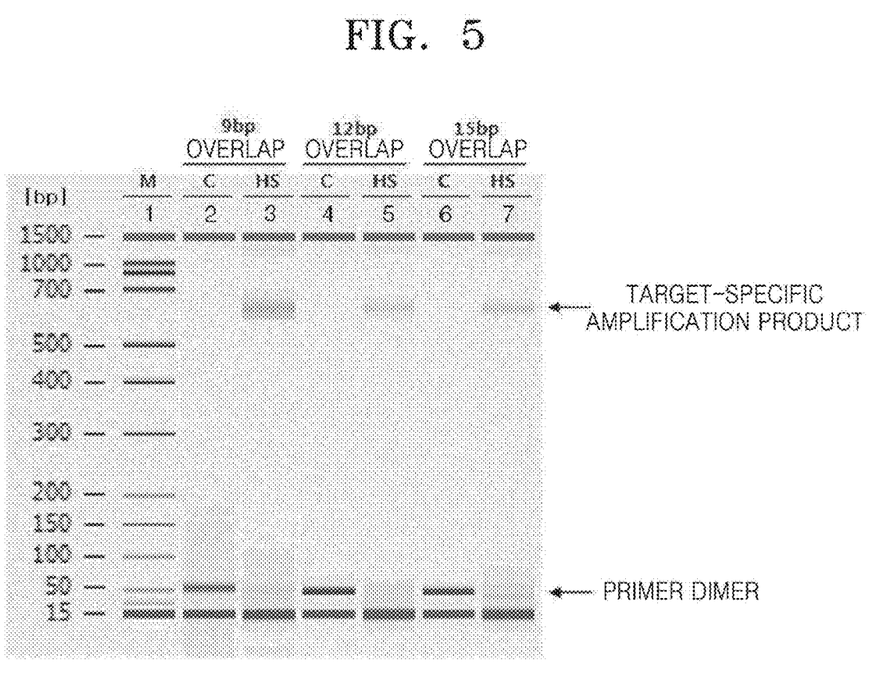
FIG. 5 is a gel electrophoresis separation showing the results of a target DNA which is amplified using a hot start primer or a normal primer.

After performing the PCR, the amplified reactant was then subjected to electrophoresis using Labchip®(Agilent Technologies), and the results thereof are shown in FIG. 5 (lane 1: a size marker (M), lanes 2, 4, and 6: a normal primer (C), lanes 3, 5, and 7: a hot start primer (HS), 9 bp overlap: a 9 bp overlap template, 12 bp overlap: a 12 bp overlap template, and 15 bp overlap: a 15 bp overlap template).

As shown in FIG. 5, in the case of using the normal primer, only non-specific amplification product having a length of 50 bp was generated by the primer dimer, and the template-specific amplification product was not detected (see lanes 2, 4, and 6 in FIG. 5). On the contrary, in the case of using the hot start primer, it was confirmed that the template-specific amplification product was detected with respect to the non-specific amplification product by the primer dimer (see lanes 3, 5, and 7 in FIG. 5).

Therefore, it was confirmed that the hot start primer maintains the double strand at the 3'-terminus of the polynucleotide at room temperatures and accordingly the non-specific amplification by the primer dimer is inhibited. It was also confirmed that, once the target-specific sequence was separated by heating, target-specific amplification product was generated at high temperatures in a range of about 50° C. to 60° C.

As described above, according to the one or more of the above embodiments of the present invention with respect to a polynucleotide and use thereof, the formation of primer dimer is inhibited to amplify a target nucleic acid with high sensitivity and amplification efficient. In addition, an operation time of a primer is adjustable and the design of the primer is easy, thereby facilitating the manufacture of the polynucleotide.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A method of amplifying a target nucleic acid, the method comprising:
   incubating or heating a first polynucleotide and a second polynucleotide in the presence of an endonuclease to provide a first incubated or heated reactant,
   wherein the first polynucleotide comprises:
   a first region comprising at least two consecutive nucleotides including the 5'-terminus that are complementary to at least two consecutive nucleotides of a first strand of a double-stranded target nucleic acid sequence;
   a second region located 3' of the first region comprising at least one cleavable nucleotide sequence,
   a third region located 3' of the second region that comprises a nucleotide sequence with a stem-loop structure, and
   a fourth region located 3' of the third region comprising at least two consecutive nucleotides complementary to at least two consecutive nucleotides of the 3' end of the first region,
   wherein the second polynucleotide comprises
   a first region comprising at least two consecutive nucleotides including the 5'-terminus of the second polynucleotide that are complementary to at least two consecutive nucleotides of a second strand of the double stranded target nucleic acid sequence,
   a second region located 3' of the first region comprising at least one cleavable nucleotide sequence,
   a third region located 3' of the second region that comprises a nucleotide sequence with a stem-loop structure, and
   a fourth region located 3' of the third region comprising at least two consecutive nucleotides of the 3' end of the first region,
   wherein the incubation or heating of the first polynucleotide and the second polynucleotide in the presence of the endonuclease nicks the second regions of the first polynucleotide and the second polynucleotide;
   incubating or heating the first incubated or first heated reactant to form a single-stranded first region of the first polynucleotide and a single-stranded first region of the second polynucleotide;
   incubating the single-stranded first region of the first polynucleotide, the single-stranded first region of the second polynucleotide, and a double stranded target nucleic acid to prepare a hybridized product comprising the first region of the first polynucleotide hybridized to the first strand of the target nucleic acid, and the first region of the second polynucleotide hybridized to the second strand of the target nucleic acid; and
   incubating the hybridized product in the presence of a nucleic acid polymerase to amplify the target nucleic acid.

2. The method according to claim 1, wherein the first polynucleotide and the second polynucleotide are a primer set.

3. The method according to claim 1, wherein the endonuclease is an endoribonuclease or a restriction enzyme.

4. The method according to claim 1, wherein the endonuclease is RNase HII.

5. The method according to claim 1, wherein the amplification is performed by thermal cycling.

6. The method according to claim 5, wherein the amplification performed by thermal cycling is a polymerase chain reaction (PCR).

7. The method according to claim 6, wherein the PCR is a hot start PCR.

8. The method according to claim 6, wherein the PCR is a multiplex PCR.

9. The method according to claim 1, wherein the second region is cleavable by an endonuclease or by heat.

10. The method according to claim 1, wherein the second region comprises RNA or DNA.

11. The method according to claim 1, wherein the second region comprises DNA, and the DNA comprises a restriction enzyme recognition site.

12. The method according to claim 1, wherein length of the second region is in a range of about 1 nucleotide to about 8 nucleotides.

13. The method according to claim 1, wherein the 3'-terminus of the first polynucleotide, the 3'-terminus of the second polynucleotide, or any combination thereof is chemically modified.

14. The method according to claim 13, wherein the chemical modification comprises a nucleic acid from which a hydroxyl group is removed, an inverted nucleotide, a dideoxynucleotide, a C6 amine, a C3 spacer, a C6 spacer, a C12 spacer, or any combination thereof.

* * * * *